(12) United States Patent
Restelli et al.

(10) Patent No.: US 11,401,297 B2
(45) Date of Patent: Aug. 2, 2022

(54) SYNTHESIS OF GLYCOCONJUGATE DERIVATIVES OF A BILE ACID

(71) Applicant: DIPHARMA FRANCIS S.r.L., Baranzate (IT)

(72) Inventors: Alessandro Restelli, Baranzate (IT); Philipp Carboni, Baranzate (IT); Gabriele Razzetti, Baranzate (IT)

(73) Assignee: DIPHARMA FRANCIS S.R.L., Baranzate (IT)

( * ) Notice: Subject to any disclaimer, the term of this patent is extended or adjusted under 35 U.S.C. 154(b) by 0 days.

(21) Appl. No.: 17/063,460

(22) Filed: Oct. 5, 2020

(65) Prior Publication Data

US 2021/0101926 A1 Apr. 8, 2021

(30) Foreign Application Priority Data

Oct. 7, 2019 (IT) .................. 102019000018110

(51) Int. Cl.
| | | |
|---|---|---|
| *C07J 9/00* | (2006.01) | |
| *C07B 41/10* | (2006.01) | |
| *C07B 43/06* | (2006.01) | |

(52) U.S. Cl.
CPC .............. *C07J 9/005* (2013.01); *C07B 41/10* (2013.01); *C07B 43/06* (2013.01)

(58) Field of Classification Search
CPC .... C07J 41/0061; C07J 9/005; C07B 2200/13
See application file for complete search history.

(56) References Cited

U.S. PATENT DOCUMENTS 5,556,587 A 9/1996 Funahashi et al.

FOREIGN PATENT DOCUMENTS

WO WO-200228411 A1 4/2002
WO WO-2010128472 A1 11/2010

OTHER PUBLICATIONS

Bergsrtom, S., and Norman, A., "Synthesis of Cunjugated Bile Acids. Bile Acids and Steroids 5," *Acta Chemica Scandinavica* 7(7):1126-1127, Royal Society of Chemistry, United Kingdom (1953).

Database CAPLUS on STN, Chemical Accession No. 2015:182535, English language abstract, Ye, J., et al., "Improvement of the process for sodium glycocolate," *Huagong Shikan* 28(2):18-20, Huagong Shikan Zazhishe, People's Republic of China, 2 pages (2014).

Heubi, J.E., et al., "Treatmen of bile acid amidation defects with glycoholic acid," *Hepatology* 61(1):268-274, John Wiley & Sons on behalf of the American Assoication for the Study of Liver Diseases, United States (2014).

*Primary Examiner* — Susanna Moore
(74) *Attorney, Agent, or Firm* — Sterne, Kessler, Goldstein & Fox P.L.L.C.

(57) ABSTRACT

Processes for the synthesis and purification of glycoconjugate derivatives of cholic acid of formula (I)

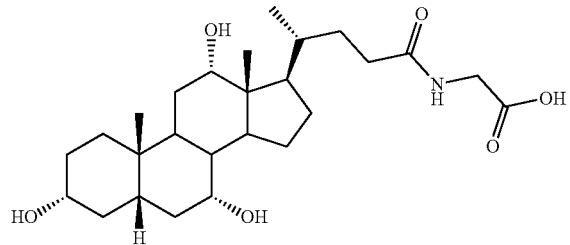

are provided herein.

17 Claims, 4 Drawing Sheets

SYNTHESIS OF GLYCOCONJUGATE DERIVATIVES OF A BILE ACID

CROSS REFERENCE TO RELATED APPLICATIONS

This application claims priority to Italian patent application No. 102019000018110, filed on Oct. 7, 2019, the entirety of which is incorporated herein by reference.

FIELD OF THE DISCLOSURE

Processes for the synthesis and the purification of glycoconjugate derivatives of cholic acid, which find use as food additives, are provided herein.

PRIOR ART

Glycocholic acid with the following formula (I)

is a bile acid present in our organism as sodium salt and is involved in the emulsification of fats. For this reason, it is used as food additive to facilitate the absorption of fat.

Orally administered glycocholic acid of formula (I) has been shown to be safe and effective in improving the absorption of fat soluble vitamins in children and adolescents with a genetically confirmed deficiency in bile acid CoA:amino acid N-acyl transferase (BAAT) (Hepatology 2015; 61: 268-274).

Despite their abundant presence in natural sources, for instance in the bile, glycoconjugate derivatives of cholanic acids are difficult to extract from these sources. Consequently, they are generally prepared starting from free bile acids, for example by activing the cholic acid with ethyl chloroformate and the subsequent treatment with glycine, as described by Bergstrom et al. in Acta Chem. Scand. 1953; 7: 1126-1127.

Glycocholic acid is widely used and therefore, there remains the need to find new and safe alternative methods for the preparation of the glycocholic acid of formula (I) at high yields, high purity and which is particularly suitable for an industrial production.

SUMMARY OF THE INVENTION

A first embodiment of the invention is a process for the preparation of the glycocholic acid of formula (I), or a salt thereof, (I)

comprising:
reacting cholic acid of formula (II)

with pivaloyl chloride in the presence of a base to give an activated intermediate of formula (III)

(III)

reacting the obtained activated intermediate of formula (III) with glycine or with an ester or a salt thereof;
in case of reacting with a glycine ester, hydrolyzing subsequently the ester;
isolating glycocholic acid of formula (I) and optionally salification thereof.

BRIEF DESCRIPTION OF THE FIGURES AND ANALYTICAL METHODS

Glycocholic acid of formula (I) in crystalline forms I (sesquihydrate) and II (anhydrous) were characterized by X-ray powder diffraction (XRPD), by differential scanning calorimetry (DSC) and thermogravimetry (TGA). X-ray diffraction spectra (XRPD) were collected with a Bruker D8 Advance diffractometer at the following operating conditions: CuKα radiation filtered with Nickel filter (λ=1.54 Å), scanning from 3 to 40° degrees with 2θ, with a step size of 0.02° in 2θ and 0.5 s acquisition for each position.

The DSC traces were acquired using open aluminum crucibles with the differential scanning calorimeter Mettler- Toledo DSC1 scanning the interval of 25 to 320° C. with a rate of 10° C./min. No purge gas was used.

The thermal gravimetric analyses were performed using open aluminum crucibles and a TGA/DSC1 (Mettler-Toledo) scanning the interval of 25 to 320° C. with a rate of 10° C./min.

DETAILED DESCRIPTION OF THE INVENTION

A first embodiment of the invention is a process for the preparation of the glycocholic acid of formula (I), or a salt thereof,

(I)

comprising:
reacting cholic acid of formula (II)

(II)

with pivaloyl chloride in the presence of a base to give an activated intermediate of formula (III)

(III)

reacting the obtained activated intermediate of formula (III) with glycine or with an ester or a salt thereof;
in case of reacting with a glycine ester, hydrolyzing subsequently the ester;
isolating glycocholic acid of formula (I) and optionally salification thereof.

By "comprising" herein is meant that additional steps may be taken in the processing, which do not substantially change the product produced by the reaction. The term comprising encompasses the terms "consisting of" and "consisting essentially of".

In one embodiment, a glycine salt or a glycocholic acid salt of formula (I) is a pharmaceutically acceptable salt. Examples of pharmaceutically acceptable salts include salts derived from an appropriate base, such as salts of an alkali metal (such as sodium or potassium), an alkaline earth metal (such as calcium or magnesium), ammonium and $NR'_4{}^+$, wherein each of R', which can be the same or different, is a $C_1$-$C_6$ alkyl.

The term "$C_1$-$C_6$ alkyl" refers to a straight, branched or cyclic hydrocarbon chain radical, consisting solely of carbon and hydrogen atoms, having from one to six carbon atoms. The "$C_1$-$C_6$ alkyl" group is for instance a linear or branched $C_1$-$C_4$ alkyl group. Examples include methyl, ethyl, n-propyl, isopropyl, n-butyl, sec-butyl or tert-butyl.

The base can be an organic base or an inorganic base.

In one embodiment, the organic base is a tertiary aliphatic or heteroaromatic amine, for example triethylamine, tri-n-butylamine, methyl-piperidine, ethyl-piperidine or pyridine.

In one embodiment, the organic base is triethylamine.

In one embodiment, the inorganic base is typically an inorganic base selected from the group comprising a hydroxide, carbonate or bicarbonate of an alkali metal or an alkaline earth metal, for example lithium, sodium or potassium hydroxide, sodium bicarbonate, potassium bicarbonate, sodium carbonate or potassium carbonate.

Said base may be typically used in an at least stoichiometric quantity in respect to cholic acid of formula (II).

If the case, the reaction of cholic acid of formula (II) with pivaloyl chloride can be carried out in the presence of a solvent, which can be for example a polar aprotic solvent, such as dimethylformamide, dimethylacetamide, N-methylpyrrolidone, acetonitrile or dimethylsulfoxide; or an acyclic or cyclic ether, for example methyl tert-butyl ether, tetrahydrofuran or dioxane; a chlorinated solvent, for example, dichloromethane, dichloroethane, chloroform or chlorobenzene; an apolar aprotic solvent, typically toluene; a polar protic solvent, typically a linear or branched $C_1$-$C_6$ alcohol, for example a $C_1$-$C_4$ alcohol; a tertiary amine such as triethylamine; or a mixture of two or more, such as two or three, of said solvents.

In one embodiment, the solvent is tetrahydrofuran.

The concentration of cholic acid of formula (II) in the reaction solution can be between 0.1 and 70% (w/w, weight/weight), typically between 2 and 50%, for example about 5%, 10%, 20%, 30%, or 40%.

The reaction with pivaloyl chloride may be carried out at a temperature ranging between about −5° C. and the reflux temperature of the solvent.

In one embodiment, the reaction with pivaloyl chloride may be carried out at a temperature between about −5° C. and about 10° C.

In one embodiment, the reaction with pivaloyl chloride may be carried out at a temperature between about −5° C. and about 5° C., for example at 0° C.

The reaction with pivaloyl chloride may be carried out at atmospheric pressure or under pressure in a closed reactor.

In one embodiment, cholic acid of formula (II) is first treated with a base in a solvent and then with pivaloyl chloride.

The treatment of cholic acid of formula (II) with the base in a solvent may be carried out at a temperature ranging from about 0° C. and the reflux temperature of the solvent, for example between 10 and 25° C.

In one embodiment, the treatment of cholic acid of formula (II) with the base in a solvent may be carried out at room temperature.

The reaction mixture of cholic acid of formula (II) and pivaloyl chloride providing the activated intermediate of formula (III) can be used in the subsequent reaction with glycine or with an ester thereof or a salt thereof, for example by adding an acidic or basic aqueous solution of glycine or an ester thereof to the reaction mixture comprising the activated intermediate of formula (III).

In one embodiment, the glycine ester is a $C_1$-$C_6$ alkyl ester, wherein the $C_1$-$C_6$ alkyl is as defined above.

In one embodiment, the glycine ester is a $C_1$-$C_4$ alkyl ester, such as methyl, ethyl, propyl, isopropyl or butyl, isobutyl, tert-butyl ester.

In one embodiment, the $C_1$-$C_6$ alkyl ester or $C_1$-$C_4$ alkyl ester may be optionally substituted by one or more substituents, such as from one to three substituents, which are the same or different, such as halogen, for example chlorine or fluorine; or aryl such as phenyl.

In one embodiment, the glycine ester is glycine ethyl ester hydrochloride.

The reaction of the activated intermediate of formula (III) with glycine or an ester thereof can be carried out at a temperature ranging between about −5° C. and the reflux temperature of the solvent.

In one embodiment, the reaction of the activated intermediate of formula (III) with glycine or an ester thereof can be carried out between about −5° C. and about 10° C.

In one embodiment, the reaction of the activated intermediate of formula (III) with glycine or an ester thereof can be carried out between about 0° C. and about 5° C., for example at 0° C.

If the case, the glycine ester can be hydrolysed according to known methods, for example by hydrolysis under basic conditions with an inorganic base, such as for example with aqueous solutions comprising sodium hydroxide, potassium hydroxide, magnesium hydroxide or calcium hydroxide.

The hydrolysis may be carried out by directly adding the base to the mixture at the end of the reaction between the activated intermediate of formula (III) and the glycine ester.

Alternatively, the aqueous phase of the reaction mixture can be separated and discarded. The organic phase can be concentrated, the obtained product dissolved in a solvent and the glycocholic acid ester hydrolyzed as described above. The solvent, in which the product can be dissolved, can be for example a polar aprotic solvent such as dimethylformamide, dimethylacetamide, N-methylpyrrolidone, acetonitrile or dimethylsulfoxide; or an acyclic or cyclic ether, for example methyl tert-butyl ether, tetrahydrofuran or dioxane; a chlorinated solvent, for example, dichloromethane, dichloroethane, chloroform or chlorobenzene; an apolar aprotic solvent, typically toluene; a polar protic solvent, typically a linear or branched $C_1$-$C_6$ alcohol, for example a $C_1$-$C_4$ alcohol, in particular methanol, ethanol, n-propanol, isopropanol, n-butanol or isobutanol; water or a mixture of two or more, for example two or three, of said solvents.

In one embodiment, the solvent is isopropanol.

The concentration of the organic phase can be carried out by distillation. The distillation may be carried out at ambient pressure or under reduced pressure.

The so obtained glycocholic acid of formula (I) can be isolated by known methods.

For example, the glycocholic acid of formula (I) can be precipitated from the mixture at the end of the reaction of the activated intermediate of formula (III) with glycine or from the reaction mixture after basic hydrolysis of the ester by adding a protic acid (HX) bringing the pH below 2.

In some embodiments, the protic acid (HX) can be a mineral or an organic acid.

A mineral acid can be, for example, selected from the group comprising sulfuric acid, phosphoric acid and a hydrohalic acid, for example hydrochloric acid.

In one embodiment, the protic acid (HX) is an aqueous solution of hydrochloric acid, for example at approximately 37% (w/w).

An organic acid can be, for example, selected from the group consisting of a sulfonic acid, typically camphorsulfonic acid, para-toluene sulfonic acid, methanesulfonic acid or trifluoromethanesulfonic acid; an aryl-carboxylic acid, typically benzoic acid; and a $C_1$-$C_4$ alkyl-carboxylic acid, wherein the $C_1$-$C_4$ alkyl group may be linear or branched, optionally substituted by one or more halogen atoms, such as one to three chlorine or fluorine atoms, such as acetic acid or trifluoroacetic acid.

The addition of the protic acid (HX) may be carried out at ambient temperature or at a temperature less than or equal to about 20° C., for example, ranging from about 0° C. to about 20° C. or between about 5° C. to about 10° C.; or the addition of the protic acid (FIX) may be carried out at a temperature greater than or equal to about 30° C., such as between about 30° C. and the reflux temperature of the solvent, for example at about 40° C., at about 50° C., at about 60° C. or at about 70° C.

The optional salification of glycocholic acid of formula (I) can be carried out according to known methods.

Moreover, according to a further embodiment of the present invention, the process can be carried out without any purification step by chromatography, for instance by ion-exchange chromatography, normal or reverse column chromatography.

The glycocholic acid of formula (I) obtained in accordance with the process described above after the addition of the protic acid (HX) has proved to be particularly pure, with a purity higher than 98% evaluated by HPLC analysis, for example 98.5%, 99.0%, 99.5% or higher than 99.9%.

A composition comprising glycocholic acid of formula (I) as defined above with a purity higher than 99.5% is a further embodiment of the invention.

A composition comprising glycocholic acid of formula (I) as defined above with a purity higher than 99.5% and wherein the content of cholic acid of formula (I) is lower than 0.5% is a further embodiment of the invention.

Figure 1:
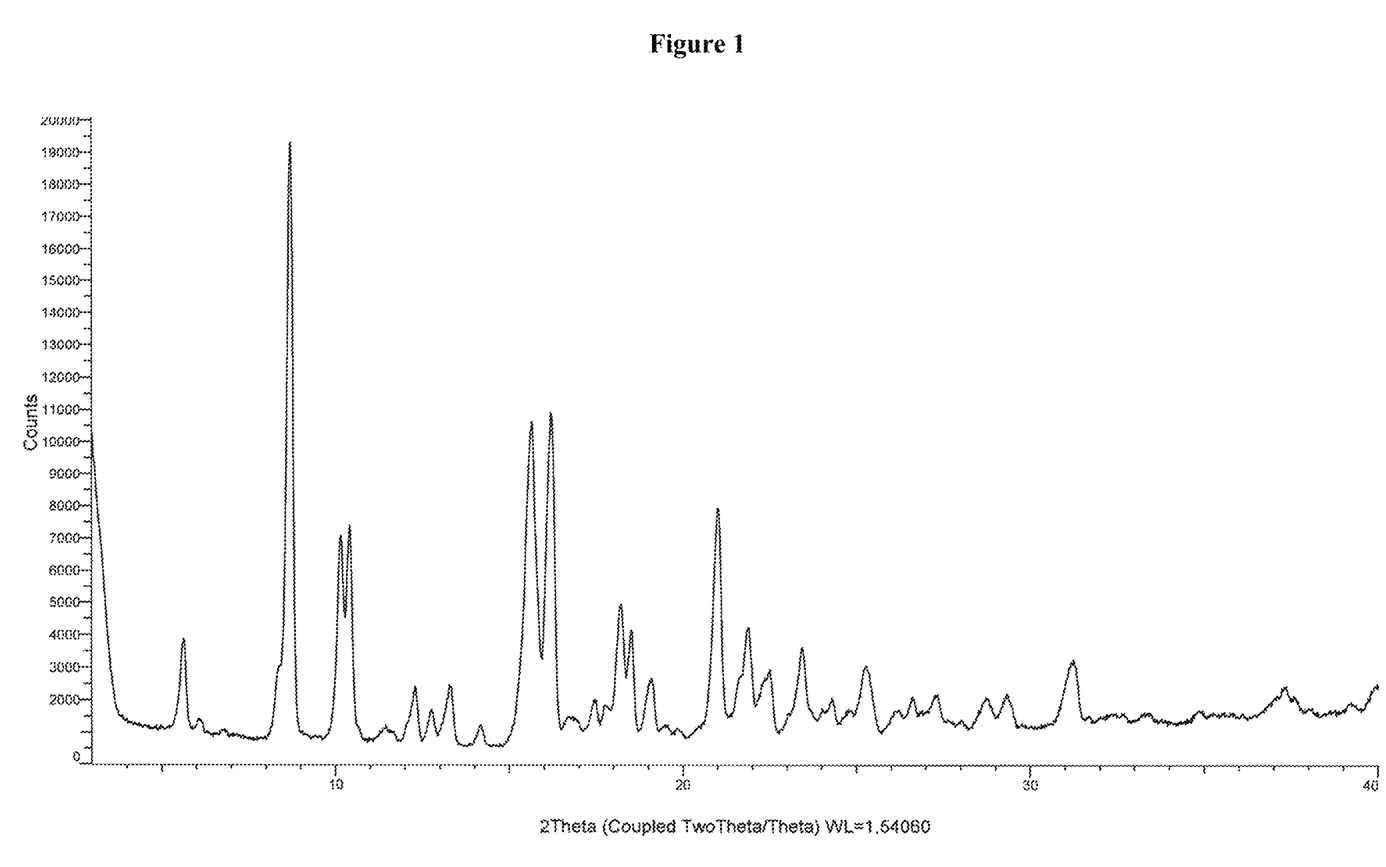
FIG. 1 shows the XRPD spectrum of glycocholic acid of formula (I) in crystalline form I (sesquihydrate).
Figure 2:
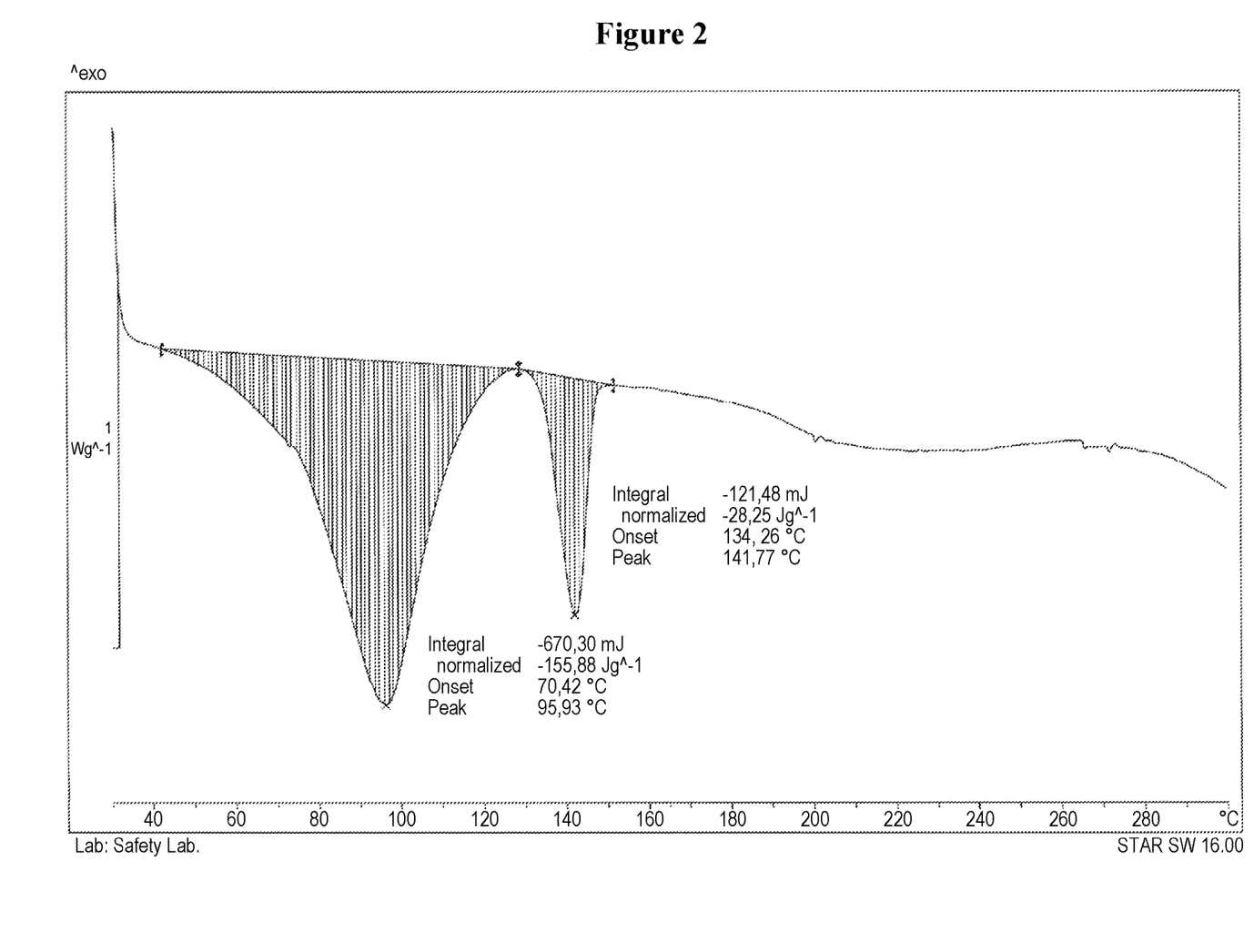
FIG. 2 shows the DSC trace of the glycocholic acid of formula (I) in crystalline form I (sesquihydrate).

In the case the protic acid (HX) is an aqueous solution of hydrochloric acid, glycocholic acid of formula (I) is obtained in crystalline form I with a water content determined by Karl Fischer method of about 5.60%, indicating that the obtained solid is a sesquihydrate. The obtained crystalline form I has an XRPD spectrum, obtained using CuKα radiation, with the characteristic peaks at 5.62; 8.69; 10.16; 10.39; 15.63; 16.20 and 21.00°±0.20° in 2θ.

The glycocholic acid of formula (I) sesquihydrate in crystalline form I with a water content determined by Karl Fischer method of about 5.60%, thus a sesquihydrate, and and having an XRPD spectrum, obtained using CuKα radiation, with the characteristic peaks at 5.62; 8.69; 10.16; 10.39; 15.63; 16.20 and 21.00°±0.20° in 2θ is a further object of the present invention.

The size of the crystals of glycocholic acid of formula (I) sesquihydrate in crystalline Form I obtained in accordance with the present process is characterized by a value of D90 between 5 and 250 µm, typically below 100 µm (Malvern Laser Diffraction Mastersizer 3000 with the Hydro 3000S measurement cell). If desired, the D90 value may be reduced by micronization or end milling.

The content of the starting compound cholic acid of formula (II) in glycocholic acid of formula (I) sesquihydrate in crystalline Form I obtained in accordance with the present process is present in a percentage lower than 0.8%, typically equal to or less than 0.5%.

Figure 3:
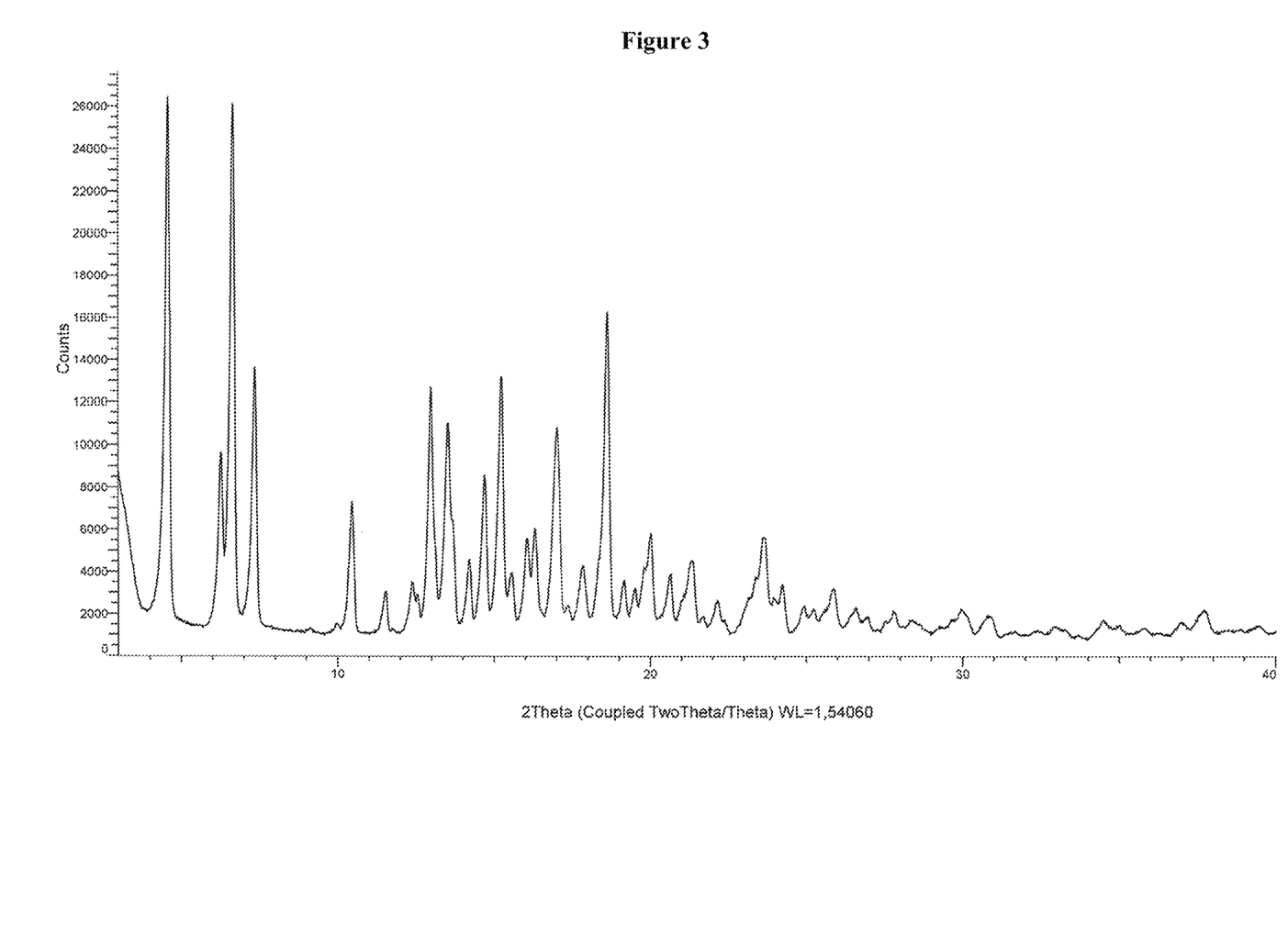
FIG. 3 shows the XRPD spectrum of glycocholic acid of formula (I) in crystalline form II (anhydrous).
Figure 4:
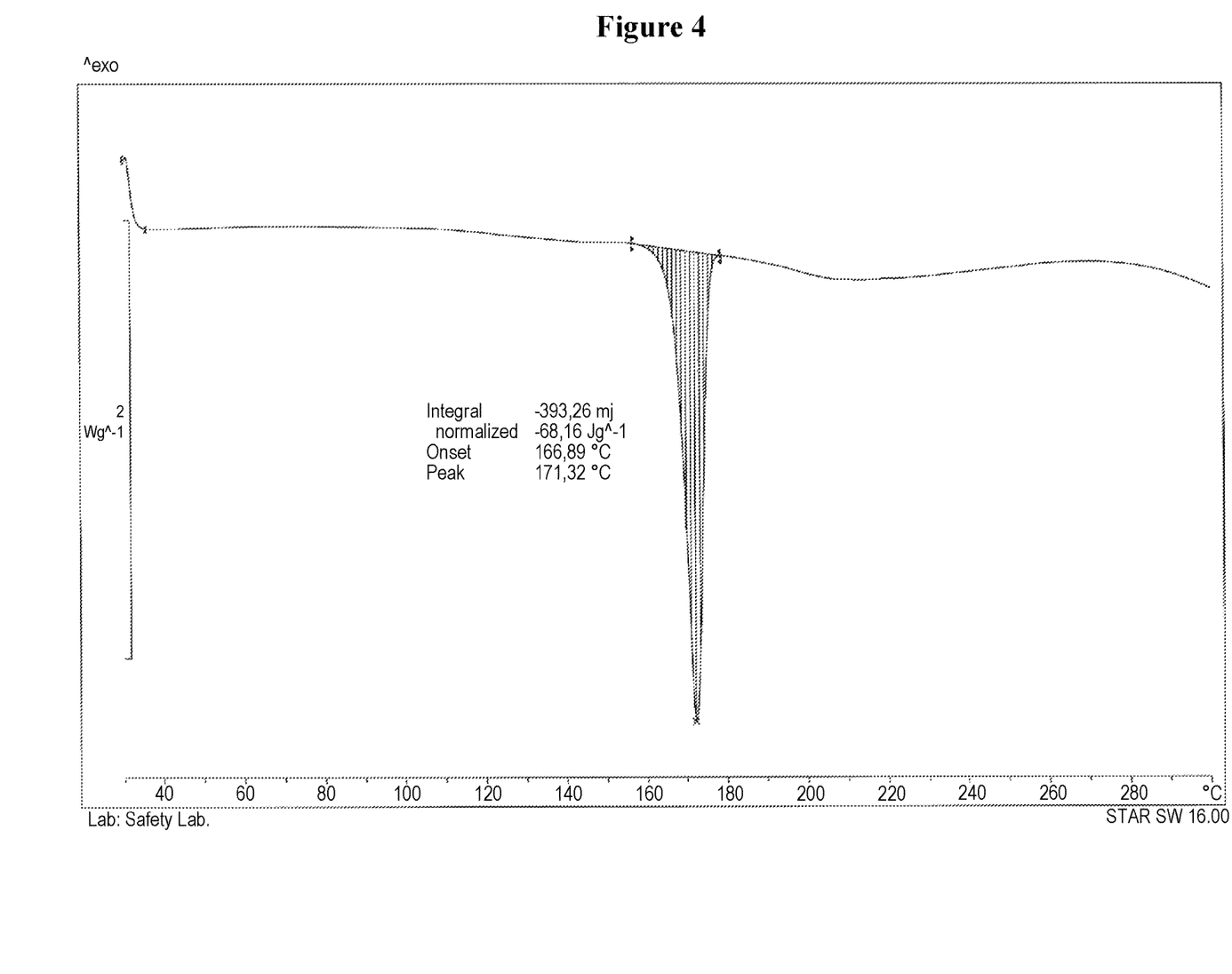
FIG. 4 shows the DSC trace of the glycocholic acid of formula (I) in crystalline form II (anhydrous).

A further embodiment of the invention provides an advantageous method for the preparation of anhydrous glycocholic acid of formula (I) in crystalline form II having an XRPD spectrum, obtained using CuKα radiation, with the characteristic peaks at 4.56; 6.64; 7.34; 10.45; 12.99; 13.53; 15.23; 17.01 and 18.62°±0.2° in 2θ, starting from sesquihydrate glycocholic acid of formula (I) sesquihydrate in crystalline form I.

According to this method, the anhydrous glycocholic acid of formula (I) in crystalline form II as defined herein can be obtained by a process comprising:

suspending glycocholic acid of formula (I) sesquihydrate in crystalline Form I and having an XRPD spectrum, obtained using CuKα radiation, with the characteristic peaks at 5.62; 8.69; 10.16; 10.39; 15.63; 16.20 and 21.00°±0.2° in 2θ in an alkyl ester of an organic acid, for example ethyl acetate or isopropyl acetate;

heating the suspension to a temperature between about room temperature and the reflux temperature of the solvent;

cooling of the suspension and isolating the anhydrous glycocholic acid of formula (I) of crystalline Form II.

In one embodiment, glycocholic acid of formula (I) sesquihydrate in crystalline Form I is suspended in ethyl acetate.

In one embodiment, the suspension can be heated typically for a time comprised between about 2 and 96 hours, for example for 5, 10, 18, 24, 36, or 48 hours.

The heating temperature is generally between 50° C. and the boiling temperature of the solvent, for example at 60° C., 70° C.

In one embodiment, the solution is then cooled down to a temperature equal to or below 50° C., for example between 0° C. and 40° C.

The anhydrous glycocholic acid of formula (I) in crystalline form II with an XRPD spectrum, obtained using CuKα radiation, with the characteristic peaks at 4.56; 6.64; 7.34; 10.45; 12.99; 13.53; 15.23; 17.01 and 18.62°±0.20° in 2θ, is a further embodiment of the present invention.

The size of the crystals of anhydrous glycocholic acid of formula (I) in crystalline form II obtained according to the present process is characterized by a value of D90 between 5 and 250 µm, typically below 100 µm (Malvern Laser Diffraction Mastersizer 3000 with the Hydro 3000S measurement cell). If desired, the D90 value may be reduced by micronization or end milling.

A compound of formula (III)

is a new compound and is a further embodiment of the invention.

A further embodiment of the invention is the use of a compound of formula (III) in the preparation of the glycocholic acid of formula (I) and the same compound of formula (III) for use in a method of preparation of the glycocholic acid of formula (I), or a salt thereof, For example, the compound of formula (III) can be converted into the glycocholic acid of formula (I) by reaction with glycine or an ester thereof or a salt thereof. In the case an ester of the amino acid glycine is used, said ester is hydrolysed providing the glycocholic acid of formula (I).

The following examples further illustrate, but do not limit, the invention.

Example 1—Synthesis of Sesquihydrate Glycocholic Acid of Formula (I) in Crystalline Form I 200 g (0.489 moles) of cholic acid of formula (II) are treated under nitrogen atmosphere with approximately 128.8 g (1.272 moles) of triethylamine in 2 L of tetrahydrofuran. The solution is stirred at 25° C. until a white solid is formed and then stirred for further 2 hours. 64.9 g (0.538 moles) of pivaloyl chloride are added to the mixture while maintaining the temperature at not more than 10° C. The obtained reaction mixture is cooled down to about 0-5° C. and 82 g (0.59 moles) of glycine ethyl ester hydrochloride in 200 ml of water are added to the mixture. After completion of the addition the mixture is allowed to reach room temperature. The aqueous phase is separated and the organic phase is washed three times with 300 ml of an aqueous solution of 2:1 NaCl 12.5% and NaHCO₃ and with 300 ml of a saturated solution of NaCl 12.5%. Then, the solvent is distilled off at reduced pressure, the obtained residue is dissolved in 416 ml of isopropanol at about 30° C. and 2.08 L (0.685 moles) of a solution of NaOH 1.3% (v:v, volume:volume) are added. The mixture is maintained at 30° C. until disappearance of the ethyl ester and then the solution is brought to a pH below 2 with concentrated HCl. After approximately 1-2 hours, the suspension is filtered, the solid washed with water and acetone and then dried in an oven under vacuum to provide 189 g (78.3% yield) of glycocholic acid of formula (I) in crystalline form I as a white solid and with a purity of 99.53% measured by HPLC. The water content determined by Karl Fischer method is about 5.60% indicating that the compound is a sesquihydrate.

XRPD main peaks in 2θ [°] (with radiation CuKα) are found at 5.62; 8.69; 10.16; 10.39; 15.63; 16.20 and 21.00°±0.20° in 2θ.

Example 2—Synthesis of Glycocholic Acid of Formula (I) Prepared According to the Procedures Disclosed in WO2010/128472

The reaction of the cholic acid of formula (I) with ethyl chloroformate and then with glycine ethyl ester hydrochloride as described in EP 2 427 473 leads to the ethylester of glycocholic acid with a yield of 82%. The yields of the subsequent purification of the raw material and the hydrolysis of the ester are 76.5% and 92.3%, respectively. The sum of the impurities present in the glycocholic acid is reported to be lower than 0.7%.

TABLE 1

Total yields of produced glycocholic acid sesquihydrate and purity data in accordance with the method described in WO2010/128472 and Example 1 of the present invention.

| Reference | Yield [%] | Purity [%] |
|---|---|---|
| WO2010/128472 | 58 | >99.3 |
| Example 1 | 78.3 | 99.53 |

Example 3—Synthesis of Anhydrous Glycocholic Acid of Formula (I) in Crystalline Form II 189 g (0.383 moles) of sesquihydrate glycocholic acid in crystalline form I of formula (I) are suspended in 2.8 l of ethyl acetate and the suspension is stirred at reflux temperature overnight. Then, the mixture is cooled down to 40° C. and the formed product is filtered off. The solid is washed with ethyl acetate and dried in an oven under vacuum providing 176.3 g (98.6% yield) of glycocholic acid of formula (I) in crystalline form II as a white solid and with a purity of 99.67% measured by HPLC. The water content determined by Karl Fischer method is approximately 0.5%.

XRPD main peaks in 2θ [°] (with radiation CuKα) are found at 4.56; 6.64; 7.34; 10.45; 12.99; 13.53; 15.23; 17.01 and 18.62°±0.20° 2θ.

Example 4—Synthesis of Glycocholic Acid of Formula (I) Prepared Using Ethyl Chloroformate or Pivaloyl Chloride The reaction of the cholic acid of formula (I) with ethyl chloroformate in THF and subsequently with glycine ethyl ester hydrochloride dissolved in water was carried out in accordance to the procedure of Example 1 taking care that the temperature during the reaction with ethyl chloroformate does not exceed 5° C. The obtained ethyl ester intermediate is treated with NaOH in accordance to the procedure of Example 1 providing glycocholic acid of formula (I) in crystalline form I as a white solid with a purity of 99.1% measured by HPLC. The content of cholic acid measured by HPLC is 0.8%, whereas the content of cholic acid in glycocholic acid of formula (I) in crystalline form I obtained according to present example 1 with pivaloyl chloride is 0.47%.

TABLE 2

Total yields of produced glycocholic acid sesquihydrate (crystalline form I), purity data as well as content of cholic acid in accordance to the reactions ethyl chloroformate and pivaloyl chloride.

| Reagent | Yield [%] | Purity [%] | Cholic Acid [%] |
|---|---|---|---|
| ethyl chloroformate | 60 | 99.1 | 0.8 |
| pivaloyl chloride | 78.3 | 99.53 | 0.47 |

As illustrated in Table 2, the reaction with pivaloyl chloride not only provides glycocholic acid of formula (I) at a yield of 78.3%, thus substantially higher than with ethyl chloroformate (60%), but also a product with a higher purity (99.53% vs. 99.1%) and a lower content of the major impurity, the starting compound cholic acid of formula (II).

The invention claimed is:

1. A process for preparing glycocholic acid of formula (I), or a salt thereof, comprising:

reacting cholic acid of formula (II)

with pivaloyl chloride in the presence of a base to give an activated intermediate of formula (III)

reacting the obtained activated intermediate of formula (III) with glycine or with an ester or a salt thereof;
in case of reacting with a glycine ester, hydrolyzing subsequently the ester;
isolating glycocholic acid of formula (I) and optionally salification thereof.

2. The process according to claim 1, wherein the base is an organic base.

3. The process according to claim 1, wherein the base is triethylamine.

4. The process according to claim 1, wherein the reaction of cholic acid of formula (II) with pivaloyl chloride is carried out in a solvent, or a mixture of two or more solvents.

5. The process according to claim 4, wherein the solvent is tetrahydrofuran.

6. The process according to claim 1, wherein the glycine ester is a $C_1$-$C_6$ alkyl ester.

7. The process according to claim 6, wherein the glycine ester is glycine ethyl ester hydrochloride.

8. The process according to claim 1, wherein the glycocholic acid of formula (I) is isolated by precipitation after adding a protic acid (HX).

9. The process according to claim 8, wherein the protic acid is an aqueous solution of hydrochloric acid, and which provides glycocholic acid of formula (I) in crystalline Form I with a water content determined by Karl Fischer method of 5.60% indicating that the obtained solid is sesquihydrate, and having an XRPD spectrum, obtained using CuKα radiation, with the characteristic peaks at 5.62; 8.69; 10.16; 10.39; 15.63; 16.20 and 21.00°±0.2° 2θ.

10. The process according to claim 9, further comprising:
suspending sesquihydrate glycocholic acid of formula (I) in crystalline Form I as defined in claim 9 in an alkyl ester of an organic acid;
heating the suspension to a temperature between about room temperature and the reflux temperature of the solvent;
cooling of the suspension and isolating the anhydrous glycocholic acid of formula (I) in crystalline Form II, wherein the anhydrous glycocholic acid of formula (I) in crystalline Form II has an XRPD spectrum, obtained using CuKα radiation, with the characteristic peaks at 4.56; 6.64; 7.34; 10.45; 12.99; 13.53; 15.23; 17.01 and 18.62°±0.2° 2θ.

11. The process according to claim 10 wherein the alkyl ester of an organic acid is ethyl acetate.

12. The process according to claim 1, wherein the process is carried out without any purification step by chromatography.

13. The process according to claim 1, wherein the base is a tertiary aliphatic or heteroaromatic amine.

14. The process according to claim 1, wherein the base is triethylamine, tri-n-butylamine, methyl-piperidine, ethyl-piperidine or pyridine.

15. The process according to claim 1, wherein the reaction of cholic acid of formula (II) with pivaloyl chloride is carried out in a polar aprotic solvent, an acyclic or cyclic ether, a chlorinated solvent, an apolar aprotic solvent, a polar protic solvent, a tertiary amine, or a mixture of two or more of said solvents.

16. The process according to claim 1, wherein the reaction of cholic acid of formula (II) with pivaloyl chloride is carried out in dimethylformamide, dimethylacetamide, N-methylpyrrolidone, acetonitrile, DMSO, methyl tert-butyl ether, tetrahydrofuran, dioxane, dichloromethane, dichloroethane, chloroform, chlorobenzene, toluene, a linear or branched $C_1$-$C_6$ alcohol, trimethylamine, or a mixture of two or more of said solvents.

17. The process according to claim 9, further comprising:
suspending sesquihydrate glycocholic acid of formula (I) in crystalline Form I as defined in claim 9 in ethyl acetate or isopropyl acetate;
heating the suspension to a temperature between about room temperature and the reflux temperature of the solvent;
cooling of the suspension and isolating the anhydrous glycocholic acid of formula (I) in crystalline Form II, wherein the anhydrous glycocholic acid of formula (I) in crystalline Form II has an XRPD spectrum, obtained using CuKα radiation, with the characteristic peaks at 4.56; 6.64; 7.34; 10.45; 12.99; 13.53; 15.23; 17.01 and 18.62°±0.2° 2θ.

* * * * *